(12) United States Patent
Maltz et al.

(10) Patent No.: US 8,416,917 B2
(45) Date of Patent: Apr. 9, 2013

(54) RADIATION THERAPY USING PREDICTIVE TARGET TRACKING AND CONTROL POINTS

(75) Inventors: Jonathan S. Maltz, Oakland, CA (US); Francisco Miguel Hernandez, Concord, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 274 days.

(21) Appl. No.: 12/849,365

(22) Filed: Aug. 3, 2010

(65) Prior Publication Data

US 2012/0033789 A1 Feb. 9, 2012

(51) Int. Cl.
*A61N 5/10* (2006.01)
(52) U.S. Cl.
USPC .......................................................... 378/65
(58) Field of Classification Search .................... 378/64, 378/65
See application file for complete search history.

(56) References Cited

U.S. PATENT DOCUMENTS

| | | | |
|---|---|---|---|
| 5,818,902 A | 10/1998 | Yu | |
| 7,469,035 B2 | 12/2008 | Keall et al. | |
| 7,609,810 B2 | 10/2009 | Yi et al. | |
| 2006/0074292 A1 | 4/2006 | Thomson et al. | |
| 2008/0144772 A1* | 6/2008 | Yi et al. | 378/65 |
| 2008/0226030 A1 | 9/2008 | Otto | |

FOREIGN PATENT DOCUMENTS

| WO | WO 2009/040117 A1 | 4/2009 |
|---|---|---|
| WO | WO 2010/062560 A2 | 6/2010 |

OTHER PUBLICATIONS

Silke Ulrich et al., "Development of an optimization concept for arc-modulated cone beam therapy", Physics in Medicine and Biology, 52 (2007), IOP Publishing, doi:10.1088/0031-9155/52/14/2006, (pp. 4099-4119, 21 pages total).
Bani-Hashemi, U.S. Appl. No. 12/834,067, entitled "Rotational Radiation Treatment of Moving Targets", filed Jul. 12, 2010.
Bani-Hashemi et al., U.S. Appl. No. 12/828,530, entitled "Radiation Treatment of Moving Targets", filed Jul. 1, 2010.
EP Search Report dated Nov. 15, 2011 from counterpart EP application No. 11174759.8-2305; 6 pages total.
Cedric X. Yu, "Intensity Modulated Arc Therapy: Technology and Clinical Implementation", AbstractID: 10351, Title: Advances in arc therapy, 2000, 14 pages.

* cited by examiner

*Primary Examiner* — Jurie Yun

(57) ABSTRACT

A system includes determination of a model of a trajectory of a target volume, determination of a treatment plan identifying a portion of the trajectory of the target volume and an irradiation field corresponding to the portion of the trajectory, the portion of the trajectory commencing at a control point of the trajectory, control of a collimator to restrict a treatment beam to the irradiation field, monitoring of the trajectory of the target volume until it is determined that the trajectory is at the control point, and delivery of the treatment beam to the irradiation field in response to determining that the trajectory of the target volume is at the control point.

9 Claims, 6 Drawing Sheets

US 8,416,917 B2

RADIATION THERAPY USING PREDICTIVE TARGET TRACKING AND CONTROL POINTS

BACKGROUND

1. Field

The embodiments described below relate generally to the delivery of therapeutic radiation to a patient. More specifically, some embodiments are directed to the delivery of radiation therapy to moving target volumes.

2. Description

According to conventional radiation therapy, a beam of radiation is directed toward a target volume (e.g., a cancerous tumor) located within a patient. The radiation beam delivers a predetermined dose of therapeutic radiation to the target volume according to an established treatment plan. The delivered radiation kills cells of the target volume by causing ionizations within the cells or other radiation-induced cell damage.

Treatment plans for delivering radiation to a patient are intended to maximize radiation delivered to a target volume, while minimizing the radiation delivered to healthy tissue. However, due to respiration and other involuntary patient motion, a target volume may move and/or change shape while a patient is positioned to receive a treatment beam.

One conventional method for delivery of radiation treatment to a moving target includes using an irradiation field that is large enough to account for target excursions from a nominal position. This method places surrounding healthy tissue or organs at an increased risk of also receiving radiation. Gated treatment involves determining a window of time during which the target movement is minimal, and to deliver a treatment beam to the target only during that window of time. Gated treatment presents an inefficient use of resources due to the significant time periods during which a treatment beam is not delivered.

Yet another proposed technique for delivering a treatment beam to a moving target uses an auxiliary device to determine the location and the shape of the target at any point in time and to continuously reshape the leaves of an MLC (multi-leaf collimator) to follow (i.e., track) the determined location and shape. However, this technique requires a dynamically-controllable (i.e., velocity and position control) collimator and sophisticated imaging and registration systems. Even so equipped, systems employing this technique have difficulty attaining desired levels of precision.

Systems are needed for delivering therapeutic radiation to moving target volumes which provide an improved treatment duty cycle (and thereby increased treatment speed), suitable accuracy, and/or simplified operation.

SUMMARY

To address at least the foregoing, some embodiments provide a system, method, apparatus, and means to determine a trajectory of a target volume, determine a treatment plan identifying a portion of the trajectory of the target volume and an irradiation field corresponding to the portion of the trajectory, where the portion of the trajectory commences at a control point of the trajectory. Also provided are control of a collimator to restrict a treatment beam to the irradiation field, monitoring of the trajectory of the target volume until it is determined that the trajectory is at the control point, and, in response to determining that the trajectory of the target volume is at the control point, delivering the treatment beam to the irradiation field.

In some aspects, determining the treatment plan includes identifying a second portion of the trajectory of the target volume and a second irradiation field corresponding to the portion of the trajectory, where the second portion of the trajectory commences at a second control point of the trajectory. Such an aspect may further include control of the collimator to restrict a second treatment beam to the second irradiation field, monitoring of the trajectory of the target volume until it is determined that the trajectory is at the second control point, and, in response to determining that the trajectory of the target volume is at the second control point, delivering a second treatment beam to the second irradiation field.

Some aspects include control of the collimator to move while delivering the treatment beam during the portion of the trajectory. According to some aspects, a model of the trajectory is determined, it is determined whether the trajectory conforms to the model of the trajectory, and delivery of the treatment beam is aborted if it is determined that the trajectory does not conform to the model of the trajectory.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

Figure 1:
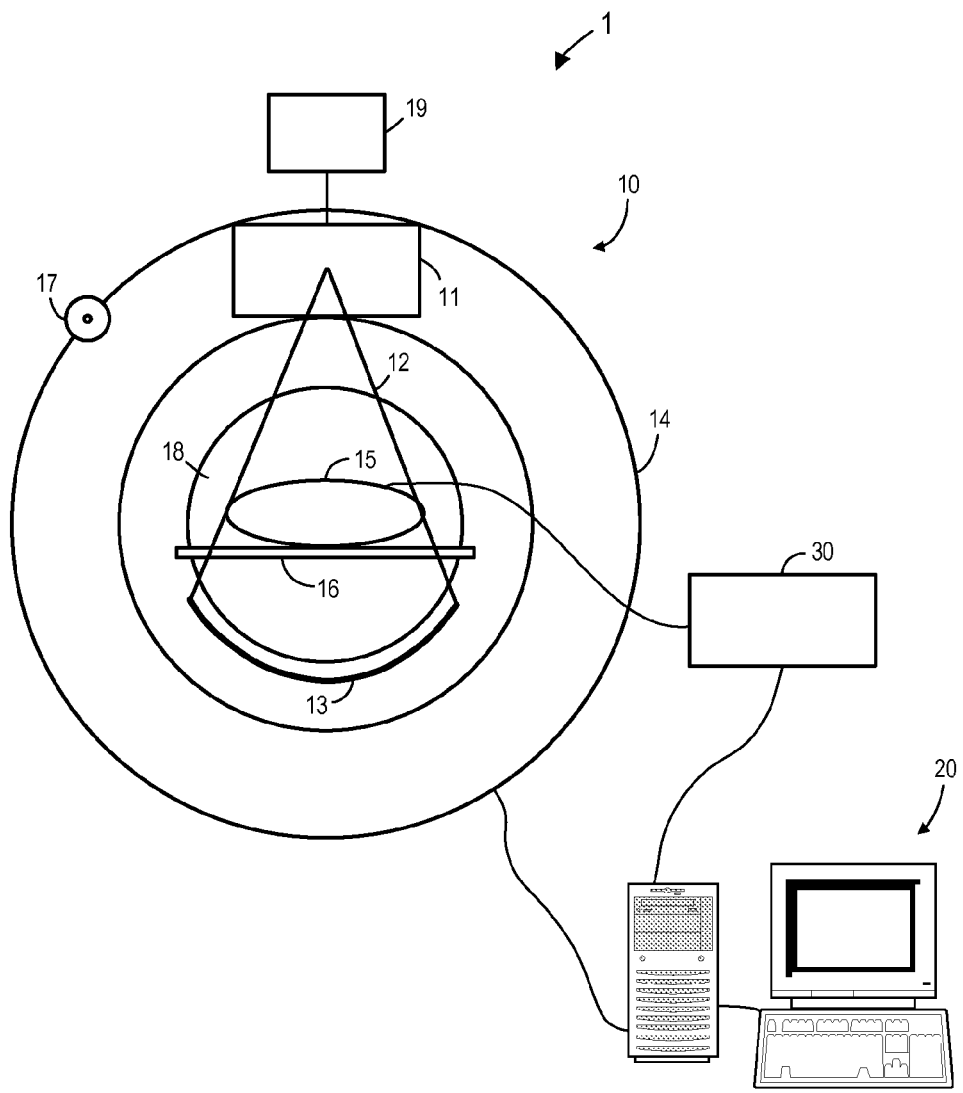
FIG. 1 illustrates a computed tomography system according to some embodiments.

The following description is provided to enable any person in the art to make and use the described embodiments and sets forth the best mode contemplated for carrying out the described embodiments. Various modifications, however, will remain readily apparent to those in the art.

A brief introduction to the features of some embodiments will be provided, followed by a discussion of systems that may be employed in the implementation of some embodiments.

Generally, in some embodiments, a trajectory of a target volume is initially determined. The trajectory may represent the motion of the target volume over time. The motion may be determined in three-dimensional space and/or in one or more two-dimensional projections along a respective angle of incidence. The trajectory may be determined via 4D fluoroscopy performed using cone-beam imaging (e.g., a linear accelerator) or CT imaging (e.g., a CT scanner) with or without fiducial markers, and/or using implanted fiducial markers whose position is detectable through non-imaging means.

The trajectory may be correlated with a patient motion cycle (e.g., respiration). More specifically, points of the trajectory may be associated with detected indicators of the patient motion cycle. In one example, a particular shape of the target volume may be determined along a particular angle of incidence when the patient is at 80% exhalation (e.g., detected via optical or contact respiration sensors).

Based on the determined trajectory, a treatment plan is developed which, for a given angle of incidence (i.e., projection angle), identifies one or more portions of the trajectory. For each of the one or more portions, the treatment plan also identifies a respective irradiation field.

Accordingly, the treatment plan calls for irradiating the target volume from a particular angle of incidence with a particularly-shaped irradiation field during a particular portion of the trajectory. The treatment plan may also call for irradiating the target volume from the particular angle of incidence with other particularly-shaped irradiation fields during other particular portions of the trajectory. The angle of incidence, the portions of the trajectory, and the irradiation fields may be selected to maximize a percentage of the trajectory during which the target volume is irradiated. The treatment plan may include one or more other angles of incidence, with respective trajectory portions and irradiation fields as described above.

Treatment delivery may proceed after the treatment plan has been determined. For example, a patient and a treatment beam delivery device are positioned so that a treatment beam delivered by the delivery device will intercept a target volume within the patient at a particular angle of incidence specified by the treatment plan. The trajectory of the target volume is monitored (directly, via imaging/fiducial detection, and/or indirectly, via a surrogate characteristic (e.g., respiration)) until the trajectory reaches a control point (i.e., the beginning of a portion of the trajectory indicated by the treatment plan). During this monitoring, a collimator of the delivery device is controlled to restrict its treatment beam to an irradiation field which the treatment plan associates with the portion of the trajectory that begins with the control point. Once the trajectory of the target volume is at the control point, the treatment beam is delivered to the irradiation field.

The above-described collimator control, monitoring and delivery may then be repeated for different portions of the trajectory. After the treatment beam has been delivered during each portion specified by the treatment plan, the treatment beam delivery device may be repositioned (e.g., by rotating a gantry attached thereto) and the above process may repeat for a new angle of incidence corresponding to the repositioned device.

The foregoing description reflects one example, and embodiments are not limited thereto. Various alternatives, additions and deletions to the above system will be described below.

FIG. 1 illustrates CT system 1. CT scanner 10 is located in a CT room and may be used to generate images of patient volumes. CT scanner 10 includes X-ray source 11 for emitting fan-shaped X-ray beam 12 toward radiation receiver 13. Both X-ray source 11 and radiation receiver 13 are mounted on ring 14 such that they may be rotated through 360 degrees while maintaining the physical relationship therebetween.

In operation, body 15 is positioned on bed 16 to place a portion of body 15 between X-ray source 11 and radiation receiver 13. Next, X-ray source 11 and receiver 13 are rotated by rotation drive 17 around cavity 18 in which body 15 lies. During this rotation, X-ray source 11 is powered by high-voltage generator 19 to transmit X-ray radiation toward receiver 13. Receiver 13 receives the radiation and produces a set of data (i.e., a projection image) for each projection angle.

Monitor 30 monitors cyclical movement of body 15. As mentioned above, monitor 30 may detect respiration of body 15 via optical or contact sensors. Computer system 20 may receive data from monitor 30 and the projection images from receiver 13. The projection images may be time-stamped during their acquisition and subsets of the images corresponding to particular phases of motion may be determined by comparing the time-stamps of the images with the data from monitor 30. A three-dimensional slice image may be reconstructed for each phase using the subset of projection images that corresponds to the phase.

System 1 may therefore produce images of a target volume over time (i.e., a trajectory) which may be used to determine a treatment plan according to some embodiments. The images may represent a cyclical trajectory that is correlated to monitorable physiological processes (e.g., respiration).

Figure 2:
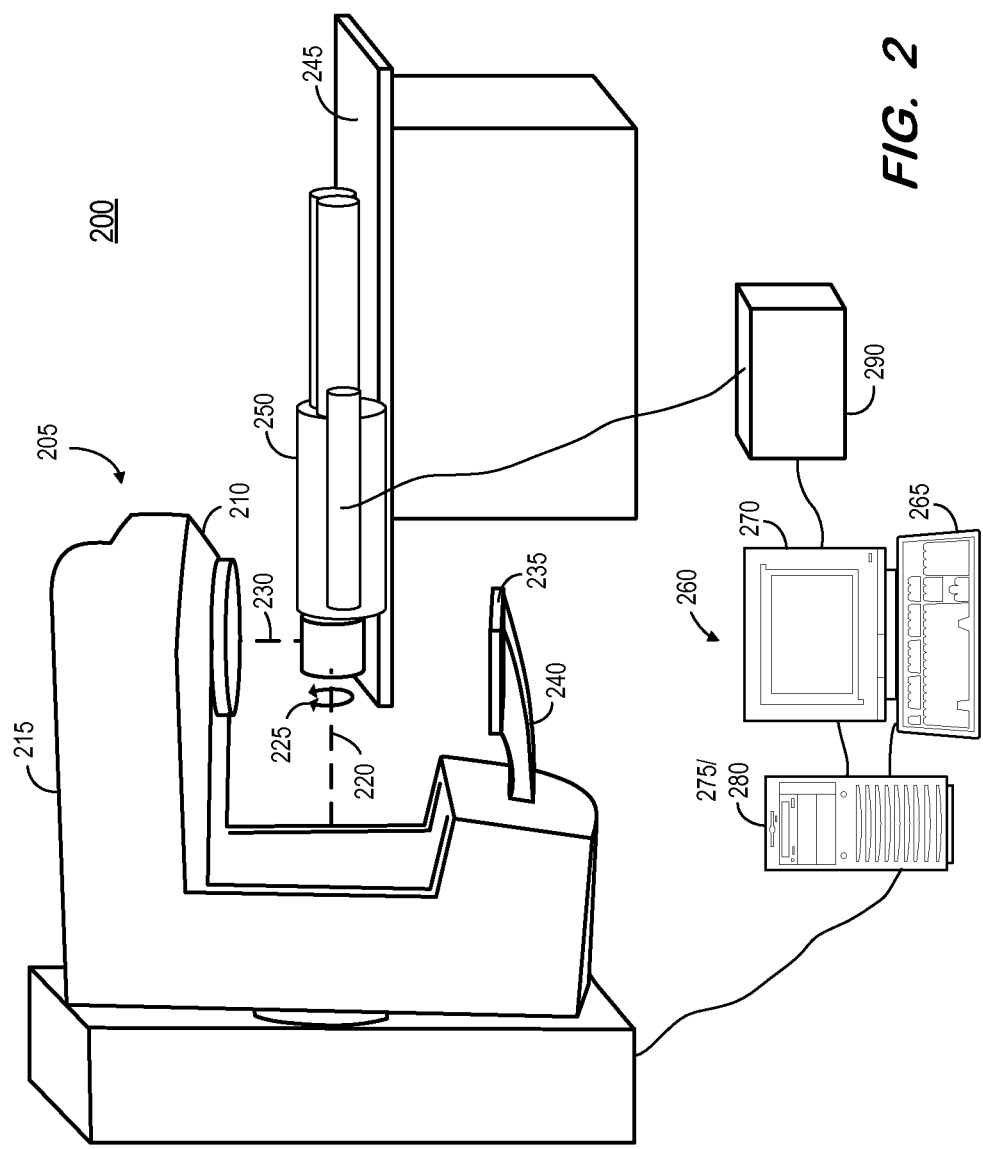
FIG. 2 is a perspective view of a radiation treatment room according to some embodiments.

FIG. 2 illustrates radiation treatment room 200 pursuant to some embodiments. Radiation treatment room 200 includes linear accelerator (linac) 205, table 245 and operator console 260. The elements of radiation treatment room 200 may be used to deliver radiation to a target volume of beam object 250. In this regard, beam object 250 may comprise a patient positioned to receive radiation according to a radiation treatment plan.

Linac 205 generates and emits the radiation, and is primarily composed of treatment head 210 and gantry 215. Treatment head 210 includes a beam-emitting device (not shown) for emitting one or more radiation beams during treatment, calibration, and/or other scenarios. An emitted radiation beam may comprise electron, photon or any other type of radiation. According to some embodiments, the radiation beam exhibits energies in the megavoltage range (i.e. >1 MeV) and may therefore be referred to as megavoltage radiation. Also included within treatment head 210 is a beam-shielding device, or collimator (not shown) for shaping the beam and for shielding sensitive surfaces from the beam.

Treatment head 210 is coupled to a projection of gantry 215. Gantry 215 is rotatable around gantry axis 220 before, during and after radiation treatment. As indicated by arrow 225, gantry 215 may rotate clockwise or counter-clockwise according to some embodiments. Rotation of gantry 215 serves to rotate treatment head 210 around axis 220.

During radiation treatment, a radiation beam is emitted from treatment head 210 as a divergent beam. The beam is emitted towards an isocenter of linac 205. The isocenter is located at the intersection of beam axis 230 and gantry axis 220. Due to divergence of the radiation beam and the shaping of the beam by the aforementioned beam-shaping devices, the beam may deliver radiation to a volume of beam object 250 rather than only to the isocenter.

Linac 205 may be operated so that each treatment beam emitted thereby exhibits a desired intensity (e.g., represented in monitor units (MU)) and aperture (i.e., a cross-sectional shape determined at least in part by the above-mentioned collimator), and is delivered from a desired gantry angle. The intensity, aperture and gantry angle of a beam are specified by a treatment plan, and control software may configure linac 205 to automatically execute such a treatment plan by delivering beams of the desired intensities and shapes from the desired angles at desired moments.

Table 245 supports beam object 250 during radiation treatment. Table 245 may be adjustable to assist in positioning a treatment area of beam object 250 at the isocenter of linac 205. Table 245 may also be used to support devices used for such positioning, for calibration and/or for verification.

Imaging device 235 may acquire images before, during and/or after radiation treatment. For example, imaging device 235 may be used to acquire images for verification and recordation of a target volume position and of an internal patient portal to which radiation is delivered.

Imaging device 235 may be attached to gantry 215 in any manner, including via extendible and retractable housing 240. Rotation of gantry 215 may cause treatment head 210 and imaging device 235 to rotate around the isocenter such that isocenter remains located between treatment head 210 and imaging device 235 during the rotation.

Imaging device 235 may comprise any system to acquire an image based on received megavoltage photon radiation. In a case that linac 205 is capable of producing kilovoltage photon radiation via beamline modification or other techniques, imaging device 235 may also acquire images based on such kilovoltage radiation. In some embodiments, imaging device 235 is a flat-panel imaging device using a scintillator layer and solid-state amorphous silicon photodiodes deployed in a two-dimensional array. In operation, the scintillator layer receives photons and generates light in proportion to the intensity of the received photons. The array of photodiodes receives the light and records the intensity of received light as stored electrical charge.

In other embodiments, imaging device 235 converts received photons to electrical charge without requiring a scintillator layer. The photons are absorbed directly by an array of amorphous selenium photoconductors. The photoconductors convert the photons directly to stored electrical charge. Imaging device 235 may also comprise a CCD or tube-based camera. Such an imaging device 235 may include a light-proof housing within which are disposed a scintillator, a mirror, and a camera.

The charge developed and stored by imaging device 235 represents radiation intensities at each location of a radiation field produced by a beam emitted from treatment head 210. Since object 250 is located between treatment head and imaging device 235, the radiation intensity at a particular location represents the attenuative properties of tissues along a divergent line between a radiation source in treatment head 210 and the particular location. The set of radiation intensities acquired by imaging device 235 may therefore comprise a two-dimensional projection image of these tissues.

Monitor 290 may monitor cyclical movement of beam object 250 as described with respect to monitor 30. The elements of treatment room 200 may therefore be used to determine a trajectory of a target volume as described above with respect to CT system 1. In particular, operator console 260 may receive data from monitor 290 and projection images from imaging device 235. The projection images may be time-stamped and subsets of the images corresponding to particular phases of motion may be determined by comparing the time-stamps of the images with the data from monitor 290. Three-dimensional slice images may be reconstructed for each phase using the subset of projection images that corresponds to the phase.

Operator console 260 includes input device 265 for receiving instructions from an operator and output device 270, which may be a monitor for presenting operational parameters of linac 205 and imaging device 235 and/or interfaces for receiving instructions. Output device 270 may also present a two-dimensional projection image, a three-dimensional megavoltage (or kilovoltage) cone beam image and/or two-dimensional "slice" images based on the three-dimensional image.

Input device 265 and output device 270 are coupled to processor 275 and storage 280. Processor 275 may execute program code to perform any of the determinations and generations described herein, and/or to cause linac 205 to perform any of the process steps described herein.

Storage 280 may also store program code to generate and/or modify a treatment plan according to some embodiments. Such code may comprise the SyngoRT™ suite or the KONRAD™ treatment planning system sold by Siemens Medical Solutions®. Accordingly, storage 280 may also store radiation treatment plans in accordance with any currently- or hereafter-known format. The treatment plans may comprise scripts that are automatically executable by elements of room 200 to provide radiation therapy fractions. Each fraction of each treatment plan may require a patient to be positioned in a particular manner with respect to treatment head 210.

Operator console 260 may be in a room other than treatment room 200, in order to protect its operator from radiation. For example, treatment room 200 may be heavily shielded, such as a concrete vault, to shield the operator from radiation generated by linac 205.

Figure 3:
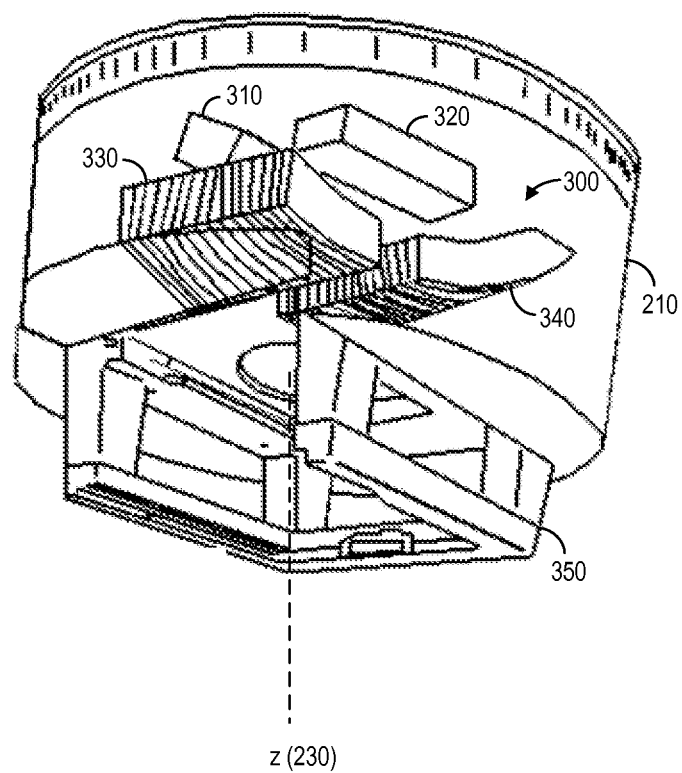
FIG. 3 is a transparent perspective view of a treatment head according to some embodiments.

FIG. 3 illustrates treatment head 210 according to some embodiments. Treatment head 210 includes collimator 300 that may be used to shape a radiation beam to conform to an aperture specified by a treatment plan. Collimator 300 includes a pair of jaws (Y-jaws) 310 and 320 and a pair of jaws (X-jaws) 330 and 340. The positioning of X-jaws 330 and 340 and Y-jaws 310 and 320 determines a size and shape of an opening through which a radiation beam may pass along axis 230.

Each pair of jaws 310/320 and 330/340 is rotatable about axis 230. As depicted in FIG. 3, X-jaws 330 and 340 may be formed of a plurality of individual elements (i.e., leaves). These individual elements may be movable along a path intersecting axis 230. Movement of each leaf may be individually-controllable to generate a wide variety of aperture shapes, resulting in a correspondingly wide variety of irradiation fields for irradiating a target volume.

As described above, elements of collimator 300 may be controlled to define an irradiation field associated with a particular portion of a target volume trajectory. According to some embodiments, the elements move during the particular portion of the trajectory such that the irradiation field is dynamic during the portion.

Treatment head 210 also includes accessory tray 350. Accessory tray 350 may be configured to receive and securely hold attachments used during the course of treatment planning and treatment (such as, for example, reticles, wedges, or the like). According to some embodiments, treatment head 210 is rotatable to rotate collimator 300 and accessory tray 350 around axis 220 without disturbing the maintaining the physical relationships between X-jaws 330 and 340, Y-jaws 310 and 320, and accessory tray 350.

Figure 4:
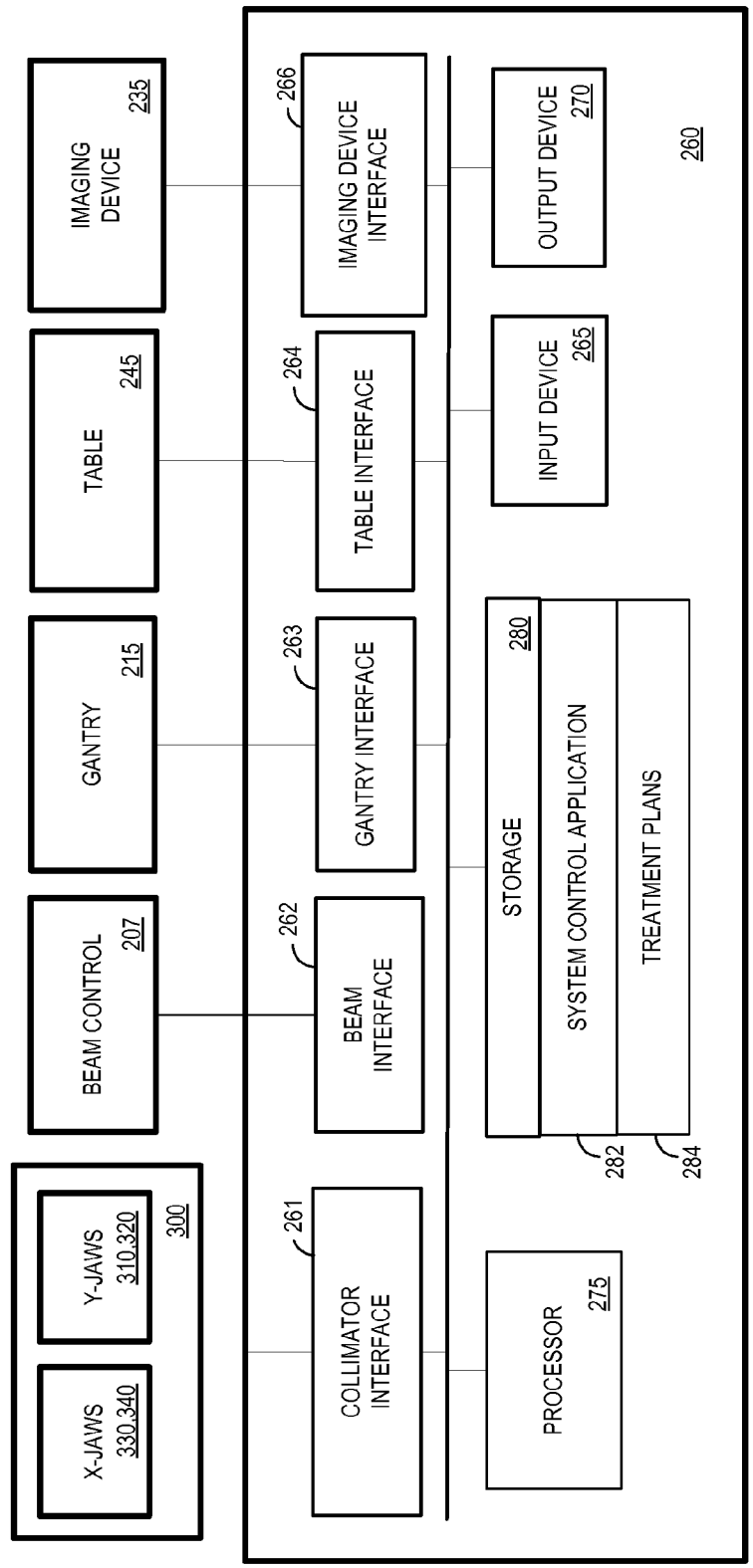
FIG. 4 is a block diagram of the internal architecture of radiation treatment room devices according to some embodiments.

FIG. 4 is a block diagram of elements of treatment room 200 according to some embodiments. The illustrated elements may be implemented by any suitable combination of hardware, software and/or firmware. Operator console 260 may be implemented by one or more separate computing systems.

As shown, operator console 260 includes several elements for interfacing with other elements of treatment room 200. Specifically, operator console 260 includes collimator interface 261, beam interface 262, gantry interface 263, table interface 264, and imaging device interface 266. Each of the interfaces may comprise any suitable type of hardware and/or software interface, and may or may not be proprietary. Operator console 260 may control the various elements through the interfaces and based on instructions from processor 275.

Collimator interface 261 may be used to control the opening and closing of each of jaws 310 through 340, the independent rotation of each pair of jaws, and/or the rotation of collimator 300. Beam interface 262 may control beam-controlling elements 207 of linac 205 based on desired beam characteristics. In particular, beam interface 262 may control trigger signals for controlling an injector current and RF power signal to generate a treatment beam having a particular energy.

Interfaces 261, 262, 263, 264 and 266 may comprise dedicated hardware and/or software interfaces, and one or more of interfaces 261, 262, 263, 264 and 266 may be implemented by a single interface. For example, interfaces 261 through 263 may be implemented by a single Ethernet interface and interfaces 264 and 266 may be implemented by proprietary interfaces for interfacing with table 245 and imaging device 235.

Processor 275 executes processor-executable process steps stored in storage 280 to provide operation according to some embodiments. These process steps may comprise system control application 282 to execute one of treatment plans 284 according to some embodiments. System control application 282 may also comprise program code to generate and/or modify one or more of treatment plans 284 as described below. A separate computer system executing the same or other software may generate a treatment plan as described below in some embodiments.

Treatment plans 284 may conform to any currently- or hereafter-known format. One of treatment plans 284 may identify one or more portions of a target volume trajectory and, for each of the one or more portions, the treatment plan may also identify a respective irradiation field. Treatment plans 284 may comprise scripts that are automatically executable by linear accelerator 205 and treatment table 245 to provide radiation therapy fractions. Each of treatment plans 284 may require a patient to be positioned in a particular manner with respect to treatment head 210.

A hardware environment according to some embodiments may include less or more elements than those shown in FIGS. 1 through 4. In addition, embodiments are not limited to the illustrated devices and/or to the illustrated environment.

Figure 5:
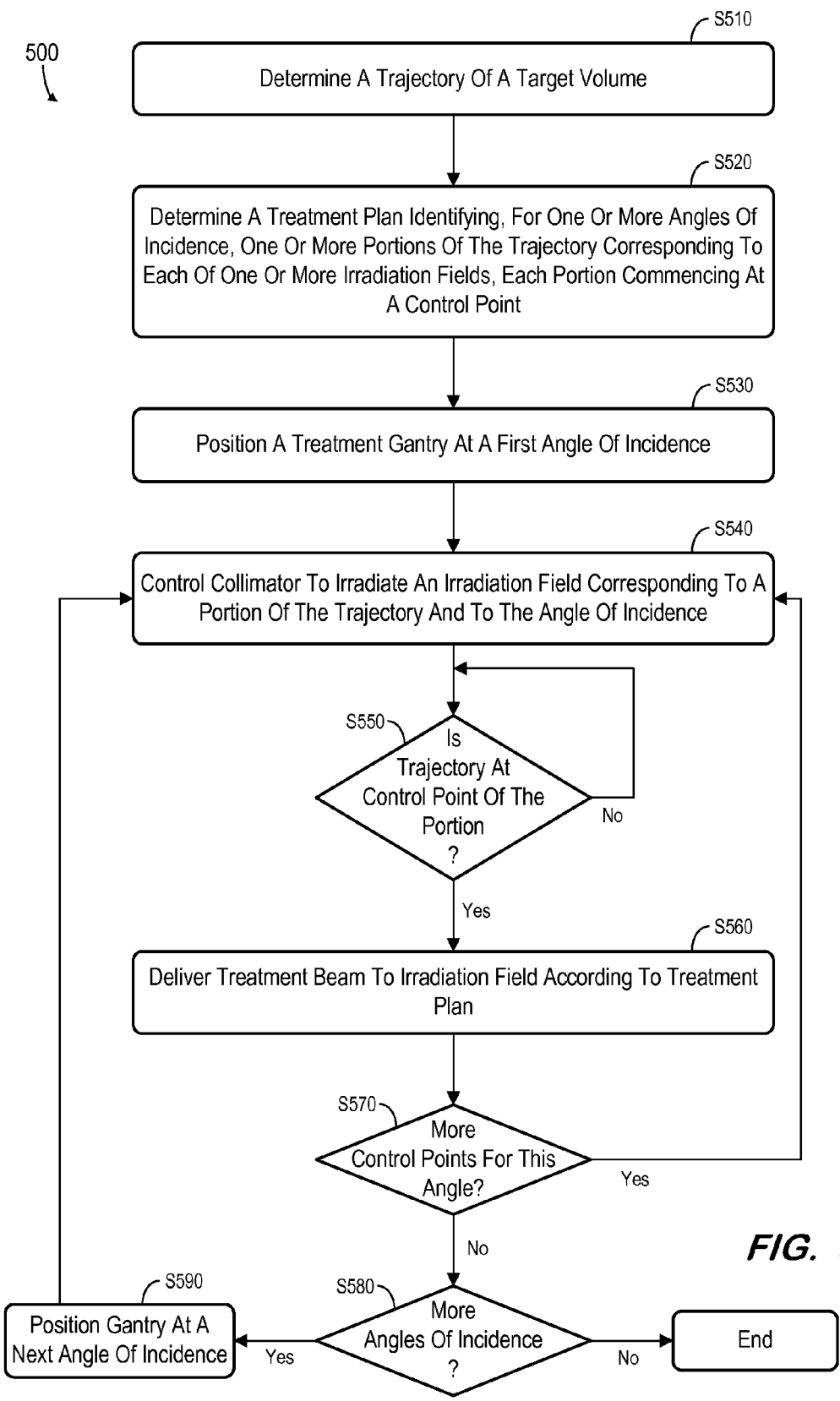
FIG. 5 comprises a flow diagram illustrating a process according to some embodiments.

FIG. 5 is a flow diagram of process 500 according to some embodiments. Process 500 and the other processes described herein may be performed using any suitable combination of hardware, software or manual means. Software embodying these processes may be stored by any tangible medium, including a fixed disk, a floppy disk, a CD-ROM, a DVD-ROM, a Flash drive, or a magnetic tape. Examples of these processes will be described below with respect to the elements of treatment room 200, but embodiments are not limited thereto.

Initially, at S510, a trajectory of a target volume is determined. The trajectory may represent the motion of the target volume over time, and may be determined in three-dimensional space and/or in one or more two-dimensional projections along a respective angle of incidence. In some embodiments, the trajectory is determined using 4D fluoroscopy in conjunction with external signal monitoring as described above with respect to FIGS. 1 and 2. As also described above, the trajectory may be determined in some embodiments using external monitoring signals and fiducial markers implanted in the target volume and detectable through non-imaging means (e.g., wireless signals, radioactive emissions).

A treatment plan is determined at S520 based on the determined trajectory. For each of one or more angles of incidence, the treatment plan identifies one or more portions of the trajectory. The treatment plan also identifies a respective irradiation field for each identified portion. The angles of incidence, the portions of the trajectory, and the irradiation fields may be selected to maximize a percentage of the trajectory during which the target volume is irradiated.

Figure 6:
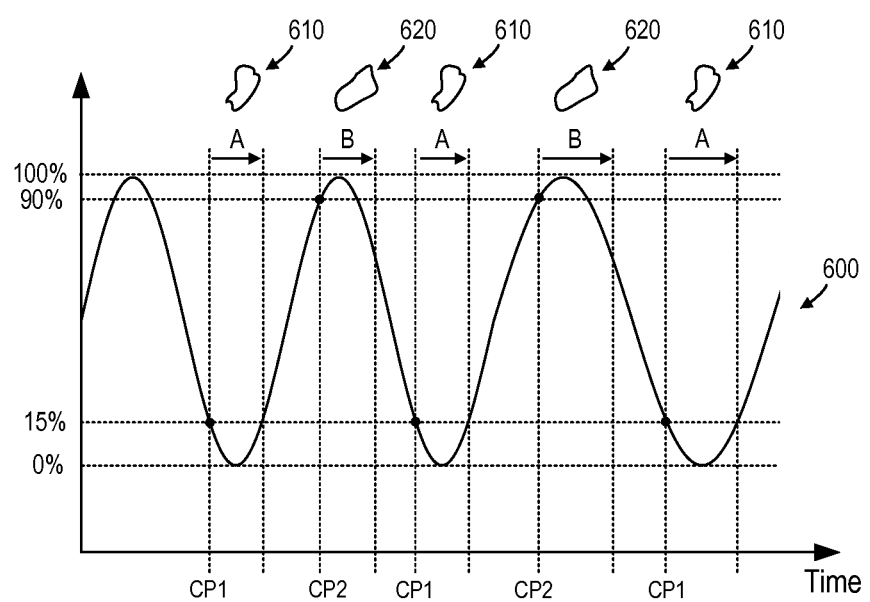
FIG. 6 is a waveform illustrating a motion cycle according to some embodiments.

FIG. 6 illustrates cycle 600 representing a physiological cycle (e.g., respiration). Cycle 600 oscillates between amplitudes representing 0% and 100% inhalation. Based on projection images of the target volume acquired at a particular projection angle and correlated to the physiological cycle as described above, portion A of cycle 600 is determined at S520 to correspond to a portion of the trajectory of the target volume which may be suitably irradiated by an irradiation field shaped as radiation field 610. As shown, portion A (and the corresponding portion of the trajectory) commences at control point CP1, and corresponds to 15% inhalation.

A treatment planner may further analyze the cycle-correlated images at S520 to determine that portion B of cycle 600 corresponds to a portion of the trajectory of the target volume which may be suitably irradiated by an irradiation field shaped as radiation field 620. Portion B (and the corresponding portion of the trajectory) commences at control point CP2, and corresponds to 90% inhalation. Due to the varying period of cycle 600, the duration of the trajectory portions (and resulting beam delivery) are not constant. In some embodiments, the trajectory portions of the treatment plan (and resulting beam delivery) are of fixed length (e.g., from detection of 20% inhalation to 1 second thereafter).

Embodiments are not limited to two portions as shown in FIG. 6. Additionally, the portions of the trajectory need not be fixedly tied to particular values of a surrogate signal as shown. For example, a portion of the trajectory may be defined as a middle third of a positive-going slope of the surrogate signal. In some embodiments, the irradiation field corresponding to a portion of the trajectory is dynamic. In this regard, trajectory portions may be identified at S520 in which a velocity of the target volume is less than a velocity achievable by leaves of collimator 300. Trajectory portions and corresponding irradiation fields may be determined for other projection angles as well.

Next, at S530, a treatment gantry is positioned at a first angle of incidence specified by the treatment plan. Accordingly, a treatment beam delivered by a treatment beam delivery device attached thereto will intercept the target volume at the first angle of incidence. A collimator of the delivery device is then controlled at S540 to irradiate an irradiation field corresponding to a portion of the trajectory specified by the treatment plan. For example, collimator 300 of treatment head 210 may be controlled at S540 to irradiate irradiation field 610 during a portion of the target volume trajectory corresponding to portion A of cycle 600.

Flow then pauses at S550 until it is determined that the trajectory of the target volume has reached the control point (e.g., control point CP1) associated with the portion of the trajectory. The trajectory may be monitored during S550 via any suitable system. For example, monitor 290 may provide respiration signals which allow console 260 to determine when inhalation is at 15%, and that control point CP1 has therefore been reached.

Once the trajectory of the target volume is at the control point, the treatment beam is delivered to the irradiation field at S560 according to the treatment plan. The treatment plan may specify a duration as well as an energy and dose rate for the treatment beam. According to some embodiments, the beam is delivered until a second "stoppage" control point is detected.

In some embodiments, the collimator is controlled to move while delivering the treatment beam during the portion of the trajectory. In this regard, the irradiation field corresponding to the portion of the trajectory is dynamic.

If more control points exist for the current angle of incidence, flow returns from S570 to S540 and continues as described above. For example, collimator 300 may be controlled at S540 to irradiate field 620, and flow may pause at S550 until inhalation reaches 90%. A treatment beam is delivered, which may exhibit a different energy, dose rate and/or duration as the previous treatment beam.

If it is determined that the treatment plan does not include any more control points for the current angle of incidence, it is then determined, at S580, whether the treatment plan includes additional angles of incidence. If so, the gantry is positioned at a next angle of incidence specified by the treatment plan at S590 and flow returns to S540. If not, treatment terminates.

According to some embodiments, monitoring the trajectory at S550 includes comparing the monitored trajectory with a model of the trajectory determined at S510. Comparison of the monitored trajectory and the model may proceed using any suitable algorithm. If the monitored trajectory does not conform to the model to an acceptable degree, delivery of the treatment beam, and of process 500, may be aborted.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
   determining a trajectory of a target volume;
   determining a treatment plan identifying a first portion of the trajectory of the target volume, a first angle of incidence, and a first irradiation field corresponding to the first portion of the trajectory, and identifying a second portion of the trajectory of the target volume and a second irradiation field corresponding to the second portion of the trajectory and to the first angle of incidence, the first portion of the trajectory commencing at a control point of the trajectory, and the second portion of the trajectory commencing at a second control point of the trajectory;
   positioning a treatment gantry to deliver a treatment beam to the target volume at the first angle of incidence;
   controlling a collimator to restrict the treatment beam to the first irradiation field;
   after controlling the collimator to restrict the treatment beam to the first irradiation field, monitoring the trajectory of the target volume until it is determined that the trajectory is at the first control point;
   in response to determining that the trajectory of the target volume is at the first control point, delivering the treatment beam to the first irradiation field at the first angle of incidence;
   controlling the collimator to restrict the treatment beam to the second irradiation field;
   after controlling the collimator to restrict the treatment beam to the second irradiation field, monitoring the trajectory of the target volume until it is determined that the trajectory is at the second control point; and
   in response to determining that the trajectory of the target volume is at the second control point, delivering the treatment beam to the second irradiation field at the first angle of incidence.

2. A method according to claim 1,
   wherein the first irradiation field corresponding to the first portion of the trajectory is dynamic, and
   wherein delivering the treatment beam to the first irradiation field comprises controlling the collimator to move while delivering the treatment beam during the first portion of the trajectory.

3. A method according to claim 1, wherein determining the trajectory comprises determining a model of the trajectory, and wherein monitoring the trajectory of the target volume comprises determining whether the trajectory conforms to the model of the trajectory, the method further comprising:
   aborting delivery of the treatment beam if it is determined that the trajectory does not conform to the model of the trajectory.

4. A non-transitory tangible medium storing processor executable program code, the program code executable by a processor to cause a system to:
   determine a trajectory of a target volume;
   determine a treatment plan identifying a first portion of the trajectory of the target volume, a first angle of incidence, and a first irradiation field corresponding to the first portion of the trajectory, and identifying a second portion of the trajectory of the target volume and a second irradiation field corresponding to the second portion of the trajectory and to the first angle of incidence, the first portion of the trajectory commencing at a control point of the trajectory, and the second portion of the trajectory commencing at a second control point of the trajectory;
   position a treatment gantry to deliver a treatment beam to the target volume at the first angle of incidence;
   control a collimator to restrict the treatment beam to the first irradiation field;
   after control of the collimator to restrict the treatment beam to the first irradiation field, monitor the trajectory of the target volume until it is determined that the trajectory is at the first control point;
   deliver the treatment beam to the first irradiation field at the first angle of incidence in response to determining that the trajectory of the target volume is at the first control point;
   control of the collimator to restrict the treatment beam to the second irradiation field;
   after control of the collimator to restrict the treatment beam to the second irradiation field, monitor the trajectory of the target volume until it is determined that the trajectory is at the second control point; and
   deliver the treatment beam to the second irradiation field at the first angle of incidence in response to determining that the trajectory of the target volume is at the second control point.

5. A medium according to claim 4,
   wherein the first irradiation field corresponding to the first portion of the trajectory is dynamic, and
   wherein delivery of the treatment beam to the first irradiation field comprises controlling the collimator to move while delivering the treatment beam during the first portion of the trajectory.

6. A medium according to claim 4, wherein determination of the trajectory comprises determination of a model of the trajectory, and wherein monitoring of the trajectory of the target volume comprises determination of whether the trajectory conforms to the model of the trajectory, the program code further executable by the processor to cause the system to:
   abort delivery of the treatment beam if it is determined that the trajectory does not conform to the model of the trajectory.

7. A system comprising:
   a treatment beam delivery device including a collimator;

a treatment gantry coupled to the treatment beam delivery device; a processor to:
  determine a trajectory of a target volume;
  determine a treatment plan identifying a first portion of the trajectory of the target volume, a first angle of incidence, and a first irradiation field corresponding to the first portion of the trajectory, and identifying a second portion of the trajectory of the target volume and a second irradiation field corresponding to the second portion of the trajectory and to the first angle of incidence, the first portion of the trajectory commencing at a control point of the trajectory, and the second portion of the trajectory commencing at a second control point of the trajectory;
move the treatment gantry to position the treatment beam delivery device to deliver a treatment beam to the target volume at the first angle of incidence;
control the collimator to restrict the treatment beam to the first irradiation field;
after control of the collimator to restrict the treatment beam to the first irradiation field, monitor the trajectory of the target volume until it is determined that the trajectory is at the first control point; control the treatment beam delivery device to deliver the treatment beam to the first irradiation field at the first angle of incidence in response to the determination that the trajectory of the target volume is at the first control point;
control the collimator to restrict the treatment beam to the second irradiation field;
after control of the collimator to restrict the treatment beam to the second irradiation field, monitor the trajectory of the target volume until it is determined that the trajectory is at the second control point; and
control the treatment beam delivery device to deliver the treatment beam to the second irradiation field at the first angle of incidence in response to the determination that the trajectory of the target volume is at the second control point.

8. A system according to claim 7,
  wherein the first irradiation field corresponding to the first portion of the trajectory is dynamic, and
  wherein the collimator moves while the treatment beam is delivered during the first portion of the trajectory.

9. A system according to claim 7, wherein determination of the trajectory comprises determination of a model of the trajectory, and wherein monitoring of the trajectory of the target volume comprises determination of whether the trajectory conforms to the model of the trajectory, and
  wherein the processor controls the treatment delivery device to abort delivery of the treatment beam if it is determined that the trajectory does not conform to the model of the trajectory.

* * * * *